(12) United States Patent
Clark et al.

(10) Patent No.: US 7,022,706 B2
(45) Date of Patent: Apr. 4, 2006

(54) PHARMACEUTICAL COMPOSITIONS AND METHODS FOR USE

(75) Inventors: Thomas Jeffrey Clark, High Point, NC (US); Balwinder Singh Bhatti, Winston-Salem, NC (US)

(73) Assignee: Targacept, Inc., Winston-Salem, NC (US)

(*) Notice: Subject to any disclaimer, the term of this patent is extended or adjusted under 35 U.S.C. 154(b) by 181 days.

(21) Appl. No.: 10/668,692

(22) Filed: Sep. 23, 2003

(65) Prior Publication Data

US 2004/0152723 A1 Aug. 5, 2004

Related U.S. Application Data

(63) Continuation of application No. 09/633,156, filed on Aug. 4, 2000, now Pat. No. 6,624,167.

(51) Int. Cl.
*C07D 471/08* (2006.01)
*C07D 487/08* (2006.01)
*A61K 31/439* (2006.01)
*A61K 31/407* (2006.01)
*A61P 25/00* (2006.01)

(52) U.S. Cl. .............. 514/252.05; 514/256; 514/314; 514/378; 514/413; 514/255.05; 544/238; 544/242; 544/336; 546/169; 546/173; 546/176; 546/180; 546/276.7

(58) Field of Classification Search ............ 514/252.05, 514/255.05, 413, 376, 314, 256; 548/245, 548/248, 452; 544/238, 242, 336; 546/168, 546/169, 173, 176, 180, 276.7
See application file for complete search history.

(56) References Cited

U.S. PATENT DOCUMENTS

| | | | | |
|---|---|---|---|---|
| 5,510,355 A | 4/1996 | Bencherif et al. | ...... | 514/305 |
| 5,817,679 A | 10/1998 | Shen et al. | ...... | 514/339 |
| 5,852,041 A | 12/1998 | Cosford et al. | ...... | 514/351 |
| 5,922,723 A | 7/1999 | Bencherif et al. | ...... | 514/256 |
| 5,952,339 A | 9/1999 | Bencherif et al. | ...... | 514/294 |
| 6,022,868 A | 2/2000 | Olesen et al. | ...... | 514/210 |
| 6,060,473 A | 5/2000 | Shen et al. | ...... | 514/253 |

FOREIGN PATENT DOCUMENTS

| | | |
|---|---|---|
| JP | 7-61940 | 3/1995 |
| WO | WO 96/06093 | 2/1996 |
| WO | WO 97/11072 | 3/1997 |
| WO | WO 97/13770 | 4/1997 |
| WO | WO 98/54182 | 12/1998 |
| WO | WO 00/44755 | 8/2000 |
| WO | WO 00/58311 | 10/2000 |
| WO | WO 01/32264 | 5/2001 |
| WO | WO 01/49690 | 7/2001 |

OTHER PUBLICATIONS

Barlocco, et al., "Mono- and Disubstituted-3-8-diazabicyclo[3.2.1.]octane Derivatives as Analgesics Structurally Related to Epibatidine: Synthesis, Activity, and Modeling," J. Med. Chem, vol. 41, 1998, pp. 674–681.

Cheng, et al., "Synthesis and binding of 6,7,8, 9-tetrahydro-5H-pyrido[3,4-d]azepine and related ring-opened analogs at central nicotinic receptors," Eur. J. Med. Chem., vol. 34, 1999, pp. 177–190.

Williams, et al., "Neuronal Nicotinic Acetylcholine Receptors," DN&P, vol. 7, No. 4, May 1994, pp. 205–223.

Badio, et al., "Synthesis and nicotine activity of epiboxidine: an isoxazole analogue of epibatidine," European Journal of Pharmacology, vol. 321, No. 2, 1997, pp. 189–194.

Olivo, et al., "Syntheses of New Open–Ring and homo–Epibatidine Analogues from Tropinone," J Org Chem. Jun. 25, 1999;64(13):4966–4968.

Lieske, Spencer F., et al., Substituted Ecgonine Methyl Esters as Inhibitors for Cocaine Binding and Dopamine Uptake, J. Med. Chem. (1998) 41(6), 864–876.

Kozikowski, A. P., et al., Chemistry and Biology of the 2-beta-Alkyl-3-beta-phenyl Analogues of Cocaine: Subnanomolar Affinity Ligands That Suggest a New Pharmacophore Model at the C-2 Position, J. Med. Chem., vol. 38, No. 16, 1995, pp. 3086–3093.

Ran, Yunzhang, et al., Studies on anticholinergics: synthesis of 3-substituted tropane derivatives retrieved from STN, abstract and RN 98042, 91-2 & Yaoxue Xuebao (1984), 19(5), 361–6.

Koh, Jong Sung, et al., Palladium-Mediated Three-Component Coupling Strategy for the Solid-Phase Synthesis of Tropane Derivatives, J. Org. Chem., (1996), 61(14), 4494–4495.

JP 07 061940 A (EISAI) Mar. 7, 1995—English Abstract Only.

*Primary Examiner*—Mark L. Berch
*Assistant Examiner*—Kahsay Habte
(74) *Attorney, Agent, or Firm*—Womble Carlyle Sandridge & Rice PLLC

(57) ABSTRACT

Pharmaceutical compositions incorporate compounds that are capable of affecting nicotinic cholinergic receptors. A wide variety of conditions and disorders, and particularly conditions and disorders associated with dysfunction of the central and autonomic nervous systems can be treated using pharmaceutical compositions incorporating compounds in which an aromatic ring is bridged with an ethylenic or acetylenic unit to an azabicyclic moiety.

38 Claims, No Drawings

PHARMACEUTICAL COMPOSITIONS AND METHODS FOR USE

This application is a continuation of U.S. Ser. No. 09/633,156 filed on Aug. 4, 2000, now U.S. Pat. No. 6,624,167, the contents of which are incorporated herein by reference.

BACKGROUND OF THE INVENTION

The present invention relates to pharmaceutical compositions, and particularly pharmaceutical compositions incorporating compounds that are capable of affecting nicotinic cholinergic receptors. More particularly, the present invention relates to compounds capable of activating nicotinic cholinergic receptors, for example, as agonists of specific nicotinic receptor subtypes. The present invention also relates to methods for treating a wide variety of conditions and disorders, and particularly conditions and disorders associated with dysfunction of the central and autonomic nervous systems.

Nicotine has been proposed to have a number of pharmacological effects. See, for example, Pullan et al. N. Engl. J. Med. 330:811–815 (1994). Certain of those effects may be related to effects upon neurotransmitter release. See for example, Sjak-shie et al., Brain Res. 624:295 (1993), where neuroprotective effects of nicotine are proposed. Release of acetylcholine and dopamine by neurons, upon administration of nicotine, has been reported by Rowell et al., J. Neurochem. 43: 1593 (1984); Rapier et al., J. Neurochem. 50: 1123 (1988); Sandor et al., Brain Res. 567: 313 (1991) and Vizi, Br. J. Pharmacol. 47: 765 (1973). Release of norepinephrine by neurons, upon administration of nicotine, has been reported by Hall et al., Biochem. Pharmacol. 21: 1829 (1972). Release of serotonin by neurons, upon administration of nicotine, has been reported by Hery et al., Arch. Int. Pharmacodyn. Ther. 296: 91 (1977). Release of glutamate by neurons, upon administration of nicotine, has been reported by Toth et al., Neurochem Res. 17: 265 (1992). In addition, nicotine reportedly potentiates the pharmacological behavior of certain pharmaceutical compositions used for the treatment of certain disorders. See, Sanberg et al., Pharmacol. Biochem. & Behavior 46: 303 (1993); Harsing et al., J. Neurochem. 59: 48 (1993) and Hughes, Proceedings from Intl. Symp. Nic. S40 (1994). Furthermore, various other beneficial pharmacological effects of nicotine have been proposed. See, Decina et al., Biol. Psychiatry 28: 502 (1990); Wagner et al., Pharmacopsychiatry 21: 301 (1988); Pomerleau et al., Addictive Behaviors 9: 265 (1984); Onaivi et al., Life Sci. 54(3): 193 (1994); Tripathi et al., JPET 221: 91–96 (1982) and Hamon, Trends in Pharmacol. Res. 15: 36.

Various nicotinic compounds have been reported as being useful for treating a wide variety of conditions and disorders. See, for example, Williams et al. DN&P 7(4): 205–227 (1994), Arneric et al., CNS Drug Rev. 1(1): 1–26 (1995), Arneric et al., Exp. Opin. Invest. Drugs 5(1): 79–100 (1996), Bencherif et al., JPET 279: 1413 (1996), Lippiello et al., JPET 279: 1422 (1996), Damaj et al., Neuroscience (1997), Holladay et al., J. Med. Chem 40(28): 4169–4194 (1997), Bannon et al., Science 279: 77–80 (1998), Japan Patent 7061940 to Kozo et al., PCT WO 94/08992, PCT WO 96/31475, PCT WO 96/40682, PCT WO 97/11072, U.S. patent application Ser. No. 09/210,113, filed on Dec. 11, 1998 and Ser. No. 09/327,141, filed Jun. 7, 1999, and U.S. Pat. No. 5,583,140 to Bencherif et al., U.S. Pat. No. 5,597,919 to Dull et al. U.S. Pat. No. 5,604,231 to Smith et al., U.S. Pat. Nos. 5,817,679, 5,852,041 to Cosford et al. and U.S. Pat. No. 6,060,473 to Shen et al. Nicotinic compounds are reported as being particularly useful for treating a wide variety of Central Nervous System (CNS) disorders.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a dopaminergic deficiency, an adrenergic deficiency and/or a serotonergic deficiency. CNS disorders of relatively common occurrence include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

It would be desirable to provide a useful method for the prevention and treatment of a condition or disorder by administering a nicotinic compound to a patient susceptible to or suffering from such a condition or disorder. It would be highly beneficial to provide individuals suffering from certain disorders (e.g., CNS diseases) with interruption of the symptoms of those disorders by the administration of a pharmaceutical composition containing an active ingredient having nicotinic pharmacology and which has a beneficial effect (e.g., upon the functioning of the CNS), but which does not provide any significant associated side effects. It would be highly desirable to provide a pharmaceutical composition incorporating a compound which interacts with nicotinic receptors, such as those which have the potential to effect the functioning of the CNS, but which compound when employed in an amount sufficient to effect the functioning of the CNS, does not significantly effect those receptor subtypes which have the potential to induce undesirable side effects (e.g., appreciable activity at skeletal muscle sites).

SUMMARY OF THE INVENTION

The present invention relates to compounds in which an aromatic ring is bridged with an ethylenic or acetylenic unit to an azabicyclic moiety. Of particular interest are compounds such as (E)-5-(2-(7-azabicyclo[2.2.1]hept-2-yl) ethenyl)isoxazole and (E)-2-(2-(3-pyridyl)ethenyl)-7-azabicyclo[2.2.1]heptane. The present invention also relates to prodrug derivatives of the compounds of the present invention.

The present invention also relates to methods for the prevention or treatment of a wide variety of conditions or disorders, and particularly those disorders characterized by disfunction of nicotinic cholinergic neurotransmission including disorders involving neuromodulation of neurotransmitter release, such as dopamine release. The present invention also relates to methods for the prevention or treatment of disorders, such as central nervous system (CNS) disorders, which are characterized by an alteration in normal neurotransmitter release. The present invention also relates to methods for the treatment of certain conditions (e.g., a method for alleviating pain). The methods involve administering to a subject an effective amount of a compound of the present invention.

The present invention, in another aspect, relates to a pharmaceutical composition comprising an effective amount of a compound of the present invention. Such a pharmaceutical composition incorporates a compound which, when employed in effective amounts, has the capability of interacting with relevant nicotinic receptor sites of a subject, and hence has the capability of acting as a therapeutic agent in the prevention or treatment of a wide variety of conditions and disorders, particularly those disorders characterized by an alteration in normal neurotransmitter release. Preferred pharmaceutical compositions comprise compounds of the present invention.

The pharmaceutical compositions of the present invention are useful for the prevention and treatment of disorders, such as CNS disorders, which are characterized by an alteration in normal neurotransmitter release. The pharmaceutical compositions provide therapeutic benefit to individuals suffering from such disorders and exhibiting clinical manifestations of such disorders in that the compounds within those compositions, when employed in effective amounts, have the potential to (i) exhibit nicotinic pharmacology and affect relevant nicotinic receptors sites (e.g., act as a pharmacological agonist to activate nicotinic receptors), and (ii) elicit neurotransmitter secretion, and hence prevent and suppress the symptoms associated with those diseases. In addition, the compounds are expected to have the potential to (i) increase the number of nicotinic cholinergic receptors of the brain of the patient, (ii) exhibit neuroprotective effects and (iii) when employed in effective amounts do not cause appreciable adverse side effects (e.g., significant increases in blood pressure and heart rate, significant negative effects upon the gastro-intestinal tract, and significant effects upon skeletal muscle). The pharmaceutical compositions of the present invention are believed to be safe and effective with regards to prevention and treatment of a wide variety of conditions and disorders.

The foregoing and other aspects of the present invention are explained in detail in the detailed description and examples set forth below.

DETAILED DESCRIPTION OF THE INVENTION

The compounds of the present invention include compounds having the structure represented by the formula:

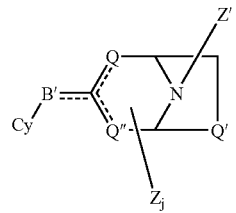

In the structure, Cy represents a suitable 5 or 6 member aromatic ring, and exemplary ring systems are set forth hereinafter. B' represents a suitable bridging moiety, such as a bridging moiety having a length of two carbon atoms (e.g., an ethylenic or acetylenic moiety). When the bridging moiety is ethylenic, the compound can have a Z (cis) or E (trans) form, but preferably the E (trans) form. Q is $(CH_2)_m$, Q' is $(CH_2)_p$, and Q" is $(CH_2)_q$ where m is 1, 2, 3 or 4 (preferably 1, 2 or 3), p is 0,1, 2 or 3 (preferably 0, 1 or 2), and q is 0, 1 or 2 (preferably 0 or 1). In addition, the values of m, p and q are selected such that the azabicyclic ring contains 6 members, or 7 members, or 8 members, or 9 members. $Z_j$ represents a suitable non-hydrogen substituent group, and exemplary groups are set forth hereinafter. In addition, j is an integer from 0 to 5, preferably 0 or 1. At the point of attachment of B' to the azabicyclic ring system, the stereochemistry of the compound can be either endo or exo. Z' is either hydrogen or lower alkyl ($C_{1-8}$), and Z' can be positioned at any location within the azabicyclic ring.

For representative compounds of the present invention, Cy includes the following:

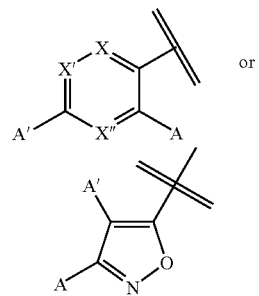

Cy can be a five member heteroaromatic ring, such as one of those described in U.S. Pat. No. 6,022,868 to Olesen et al., the disclosure of which is incorporated by reference in its entirety, which may bear suitable non-hydrogen substituent species as set forth hereinafter. Thus, as used herein, the terms "5 or 6 member aromatic ring" and "five or six member heteroaromatic ring" refer to aromatic ring systems wherein the structure of the ring is composed of either 5 or 6 members (e.g., carbon atoms, or carbon and nitrogen atoms); and those 5 or 6 member rings can possess suitable substituent moieties. Each of X, X' and X" are individually nitrogen, nitrogen bonded to oxygen (e.g., an N-oxide or N—O functionality) or carbon bonded to a substituent species characterized as having a sigma m value greater than 0, often greater than 0.1, and generally greater than 0.2, and even greater than 0.3; less than 0 and generally less than –0.1; or 0; as determined in accordance with Hansch et al., Chem. Rev. 91: 165 (1991). When any of X, X' and X" are carbon bonded to a substituent species, those substituent species typically have a sigma m value between about –0.3 and about 0.75, frequently between about –0.25 and about 0.6; and each sigma m value individually can be 0 or not equal to zero. In addition, A and A' individually are either hydrogen or suitable non-hydrogen substituent species; and typically those substituent species have a sigma m value between about –0.3 and about 0.75, frequently between about –0.25 and about 0.6; and each sigma m value individually can be 0 or not equal to zero. Preferably, 1 or 2 of X, X' and X" are nitrogen or nitrogen bonded to oxygen. In addition, it is highly preferred that not more than one of X, X' and X" be nitrogen bonded to oxygen; and it is preferred that if one of those species is nitrogen bonded to oxygen, that species is X". Typically, X' is CH, CBr, CR', or COR', where R' (defined hereinafter) preferably is benzyl, methyl, ethyl, isopropyl, isobutyl, tertiary butyl, cycloalkyl (e.g., cyclopropyl, cyclobutyl, cyclopentyl, cyclohexyl or cycloheptyl), or an unsubstituted or substituted, five or six membered, aromatic or heteroaromatic ring. Most preferably, X" is nitrogen. For certain other preferred compounds X" is C—NR'R", COR' or $CNO_2$, typically $CNH_2$, $CNHCH_3$ or $CN(CH_3)_2$, with $CNH_2$ being preferred. In certain preferred circumstances, both X' and X" are nitrogen. Typically, X is carbon bonded to a substituent species, and it is typical that X is carbon bonded to a substituent species such as hydrogen. Adjacent substituents of X, X', A', X" and A (when adjacent X, X' and X" each are carbon bonded to a respective substituent component) can combine to form one or more saturated or unsaturated, substituted or unsubstituted carbocyclic or heterocyclic rings containing, but not limited to, ether, acetal, ketal, amine, ketone, lactone, lactam, carbamate, or urea functionalities.

The substituents of either X, X' or X" (when each respective X, X' and X" is carbon), the substituents A, A' and Z, and the substituents attached to five member heteroaromatic ring representatives of unit Cy can include alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, halo (e.g., F, Cl, Br, or I), —NR'R", —CF$_3$, —OH, —CN, —NO$_2$, —C$_2$R', —SH, —SCH$_3$, —N$_3$, —SO$_2$CH$_3$, —OR', —SR', —C(=O)NR'R", —NR'C(=O)R', —C(=O)R', —C(=O)OR', —(CH$_2$)$_x$OR', —OC(=O)R', —(CR'R")$_x$OCH$_2$C$_2$R', —(CR'R")$_x$C(=O)R', —O(CR'R")$_x$C(=O)R', —C$_2$(CR'R")$_x$OR', —(CR'R")$_x$NR'R", —OC(=O)NR'R" and —NR'C(=O)OR' where R' and R" are individually hydrogen or lower alkyl (e.g., straight chain or branched alkyl including C$_1$–C$_8$, preferably C$_1$–C$_5$, such as methyl, ethyl, or isopropyl), an aromatic group-containing species or a substituted aromatic group-containing species, and x is an integer from 1 to 6. R' and R" can be straight chain or branched alkyl, or R' and R" can form a cycloalkyl functionality. Representative aromatic group-containing species include pyridinyl, quinolinyl, pyrimidinyl, phenyl, and benzyl (where any of the foregoing can be suitably substituted with at least one substituent group, such as alkyl, hydroxyl, alkoxy, halo, or amino substituents). Other representative aromatic ring systems are set forth in Gibson et al., *J. Med. Chem.* 39: 4065 (1996). The substituents of X, X' and X", the substituents A and A', and the substituents attached to five member heteroaromatic ring representatives of unit Cy individually can include hydrogen.

When B' is ethylenic, B' can be represented as —CE'=CE"-, where E' and E" individually represent hydrogen or a suitable non-hydrogen substituent (e.g., alkyl, substituted alkyl, halo substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl), preferably lower alkyl (e.g., straight chain or branched alkyl including C$_1$–C$_8$, preferably C$_1$–C$_5$, such as methyl, ethyl, or isopropyl) or halo substituted lower alkyl (e.g., straight chain or branched alkyl including C$_1$–C$_8$, preferably C$_1$–C$_5$, such as trifluoromethyl or trichloromethyl). Generally, both of E' and E" are hydrogen; or one of E' or E" is non-hydrogen (e.g., alkyl, such as methyl) and the other is hydrogen.

Compounds of the present invention can, depending on their structure, occur as stereoisomers (e.g., E/Z isomers about a double bond or R,S isomers about a chiral center). Both the bicyclic ring system and the bridging moiety (B') can be sources of stereoisomerism. The present invention relates to mixtures of stereoisomers, such as racemates, as well as single stereoisomer compounds.

As employed herein, "alkyl" refers to straight chain or branched alkyl radicals including C$_1$–C$_8$, preferably C$_1$–C$_5$, such as methyl, ethyl, or isopropyl; "substituted alkyl" refers to alkyl radicals further bearing one or more substituent groups such as hydroxy, alkoxy, mercapto, aryl, heterocyclo, halo, amino, carboxyl, carbamyl, cyano, and the like; "alkenyl" refers to straight chain or branched hydrocarbon radicals including C$_1$–C$_8$, preferably C$_1$–C$_5$ and having at least one carbon-carbon double bond; "substituted alkenyl" refers to alkenyl radicals further bearing one or more substituent groups as defined above; "cycloalkyl" refers to saturated or unsaturated, non-aromatic, cyclic ring-containing radicals containing three to eight carbon atoms, preferably three to six carbon atoms; "substituted cycloalkyl" refers to cycloalkyl radicals further bearing one or more substituent groups as defined above; "aryl" refers to aromatic radicals having six to ten carbon atoms; "substituted aryl" refers to aryl radicals further bearing one or more substituent groups as defined above; "alkylaryl" refers to alkyl-substituted aryl radicals; "substituted alkylaryl" refers to alkylaryl radicals further bearing one or more substituent groups as defined above; "arylalkyl" refers to aryl-substituted alkyl radicals; "substituted arylalkyl" refers to arylalkyl radicals further bearing one or more substituent groups as defined above; "heterocyclyl" refers to saturated or unsaturated cyclic radicals containing one or more heteroatoms (e.g., O, N, S) as part of the ring structure and having two to seven carbon atoms in the ring; "substituted heterocyclyl" refers to heterocyclyl radicals further bearing one or more substituent groups as defined above.

Of particular interest are compounds of the formulas set forth hereinbefore wherein preferably j is 0, and Z' is hydrogen or lower alkyl; preferably m is 1, 2 or 3, q is 0 or 1, and the sum of m and q is 3 or less; preferably p is 1 or 2; preferably each of E' and E" is hydrogen or methyl, but most preferably each of E' and E" is hydrogen; preferably Cy is 3-pyridyl (unsubstituted or substituted in the 5 and/or 6 position(s) with any of the aforementioned substituents), 5-pyrimidinyl (unsubstituted or substituted in the 2 position with any of the aforementioned substituents), or 3- or 5-isoxazolyl (unsubstituted or substituted in the 4 and/or 5 and 3 and/or 4 positions respectively).

Representative compounds of the present invention include the following:
(E)- and (Z)-5-(2-(7-azabicyclo[2.2.1]hept-2-yl)ethenyl)isoxazole
(E)- and (Z)-5-(2-(7-azabicyclo[2.2.1]hept-2-yl)ethenyl)-3-methylisoxazole
(E)- and (Z)-5-(2-(8-azabicyclo[3.2.1]oct-6-yl)ethenyl)isoxazole
(E)- and (Z)-5-(2-(8-azabicyclo[3.2.1]oct-6-yl)ethenyl)-3-methylisoxazole
(E)- and (Z)-5-(2-(8-azabicyclo[3.2.1]oct-2-yl)ethenyl)isoxazole
(E)- and (Z)-5-(2-(8-azabicyclo[3.2.1]oct-2-yl)ethenyl)-3-methylisoxazole
(E)- and (Z)-5-(2-(9-azabicyclo[4.2.1]non-2-yl)ethenyl)isoxazole and
(E)- and (Z)-5-(2-(9-azabicyclo[4.2.1]non-2-yl)ethenyl)-3-methylisoxazole.

The following compounds also are representative compounds of the present invention:
(E)- and (Z)-2-(2-(3-pyridyl)ethenyl)-7-azabicyclo[2.2.1]heptane
(E)- and (Z)-2-(2-(5-methoxy-3-pyridyl)ethenyl)-7-azabicyclo[2.2.1]heptane
(E)- and (Z)-2-(2-(5-ethoxy-3-pyridyl)ethenyl)-7-azabicyclo[2.2.1]heptane
(E)- and (Z)-2-(2-(5-isopropoxy-3-pyridyl)ethenyl)-7-azabicyclo[2.2.1]heptane
(E)- and (Z)-2-(2-(5-isobutoxy-3-pyridyl)ethenyl)-7-azabicyclo[2.2.1]heptane (E)- and (Z)-2-(2-(5-phenoxy-3-pyridyl)ethenyl)-7-azabicyclo[2.2.1]heptane
(E)- and (Z)-2-(2-(5-benzyloxy-3-pyridyl)ethenyl)-7-azabicyclo[2.2.1]heptane
(E)- and (Z)-2-(2-(5-methoxymethyl-3-pyridyl)ethenyl)-7-azabicyclo[2.2.1]heptane
(E)- and (Z)-2-(2-(5-phenyl-3-pyridyl)ethenyl)-7-azabicyclo[2.2.1]heptane
(E)- and (Z)-2-(2-(5-hydroxy-3-pyridyl)ethenyl)-7-azabicyclo[2.2.1]heptane
(E)- and (Z)-2-(2-(5-pyrimidinyl)ethenyl)-7-azabicyclo[2.2.1]heptane
(E)- and (Z)-2-(2-(3-pyridyl)ethenyl)-8-azabicyclo[3.2.1]octane
(E)- and (Z)-6-(2-(3-pyridyl)ethenyl)-8-azabicyclo[3.2.1]octane and
(E)- and (Z)-2-(2-(3-pyridyl)ethenyl)-9-azabicyclo[4.2.1]nonane.

The following compounds also are representative compounds of the present invention:
2-(2-(3-pyridyl)ethynyl)-7-azabicyclo[2.2.1]heptane
2-(2-(5-methoxy-3-pyridyl)ethynyl)-7-azabicyclo[2.2.1]heptane
2-(2-(5-ethoxy-3-pyridyl)ethynyl)-7-azabicyclo[2.2.1]heptane
2-(2-(5-isopropoxy-3-pyridyl)ethynyl)-7-azabicyclo[2.2.1]heptane
2-(2-(5-isobutoxy-3-pyridyl)ethynyl)-7-azabicyclo[2.2.1]heptane
2-(2-(5-phenoxy-3-pyridyl)ethynyl)-7-azabicyclo[2.2.1]heptane
2-(2-(5-benzyloxy-3-pyridyl)ethynyl)-7-azabicyclo[2.2.1]heptane
2-(2-(5-methoxymethyl-3-pyridyl)ethynyl)-7-azabicyclo[2.2.1]heptane
2-(2-(5-phenyl-3-pyridyl)ethynyl)-7-azabicyclo[2.2.1]heptane
2-(2-(5-hydroxy-3-pyridyl)ethynyl)-7-azabicyclo[2.2.1]heptane
2-(2-(5-pyrimidinyl)ethynyl)-7-azabicyclo[2.2.1]heptane
2-(2-(3-pyridyl)ethynyl)-8-azabicyclo[3.2.1]octane
6-(2-(3-pyridyl)ethynyl)-8-azabicyclo[3.2.1]octane and
2-(2-(3-pyridyl)ethynyl)-9-azabicyclo[4.2.1]nonane.

The manner in which arylethenyl- and arylethynyl-substituted 7-azabicyclo[2.2.1]heptane compounds of the present invention are synthetically produced can vary. Ethyl 7-aza-2-formylbicyclo[2.2.1]heptane-7-carboxylate can be utilized as a key intermediate in the synthetic pathway. Treatment of tropinone with ethyl chloroformate provides ethyl 8-aza-3-oxobicyclo[3.2.1]octane-8-carboxylate which is readily converted to ethyl 8-aza-2-bromo-3-oxobicyclo[3.2.1]octane-8-carboxylate upon treatment with bromine and 30% hydrogen bromide in acetic acid. Subsequent Favorski ring contraction using freshly prepared sodium ethoxide in ethanol provides ethyl 7-aza-2-(ethoxycarbonyl)bicyclo[2.2.1]heptane-7-carboxylate, as reported by Daly et al. *Eur. J. Pharmacol.* 321: 189–194 (1997). Di-isobutylaluminum hydride reduction of the ester functionality provides ethyl 7-aza-2-formylbicyclo[2.2.1]heptane-7-carboxylate in modest overall yield. Horner-Wadsworth-Emmons reaction between diethyl (5-isoxazolylmethyl)phosphonate and ethyl 7-aza-2-formylbicyclo[2.2.1]heptane-7-carboxylate provides a mixture of ethyl (E)-5-(2-(7-azabicyclo[2.2.1]hept-2-yl)ethenyl)isoxazole carboxylate and ethyl (Z)-5-(2-(7-azabicyclo[2.2.1]hept-2-yl)ethenyl)isoxazole carboxylate. The two isomers are readily separated by chromatography. Diethyl (5-isoxazolylmethyl)phosphonate is prepared according to the method described in Deshong et. al. *J. Org. Chem.* 53: 1356–1364 (1988). Deprotection of the amine functionality of ethyl (E)-5-(2-(7-azabicyclo[2.2.1]hept-2-yl)ethenyl)isoxazole carboxylate using hydrochloric acid affords (E)-5-(2-(7-azabicyclo[2.2.1]hept-2-yl)ethenyl)isoxazole. The synthesis of this compound is described as Example 1. Alternatively, the treatment of ethyl 7-aza-2-formylbicyclo[2.2.1]heptane-7-carboxylate with 5-(lithiomethyl)isoxazole and dehydration of the resulting alcohol as described in U.S. Pat. No. 6,022,868 to Olesen et. al. followed by removal of the ethyl carbamate protecting group will provide (E)- and (Z)-5-(2-(7-azabicyclo[2.2.1]hept-2-yl)ethenyl)isoxazole.

Compounds of the present invention include those in which the isoxazole ring is substituted (e.g., on the 3 and 4 position) with moieties that are stable to the processes used in their generation. For instance, treatment of ethyl 7-aza-2-formylbicyclo[2.2.1]heptane-7-carboxylate with the anion of 5-diethylphosphonylmethyl-3-methylisoxazole will provide (E) and (Z)-5-(2-(7-azabicyclo[2.2.1]hept-2-yl)ethenyl)-3-methylisoxazole in a similar manner to that described for Example 1. 5-Diethylphosphonylmethyl-3-methylisoxazole can be prepared as described in Lee et. al. *Synthetic Commun.* 29: 3621–3636 (1999) and Lee et. al. *Synthesis* 2027–2029 (1999). Alternatively, treatment of 3-methyl-5-(trimethylsilyl(lithiomethyl))isoxazole with of ethyl 7-aza-2-formylbicyclo[2.2.1]heptane-7-carboxylate followed by removal of the carbamate protecting group will provide (E)- and (Z)-5-(2-(7-azabicyclo[2.2.1]hept-2-yl)ethenyl)-3-methylisoxazole. Techniques such as those described in U.S. Pat. No. 6,022,868 to Olesen et al. can be used. Arylethenyl-substituted azabicyclic compounds containing other five-membered heterocycles can using Horner-Wadsworth-Emmons reaction chemistry as described in U.S. Pat. No. 6,022,868 to Olesen et al. Alternatively, condensation of ethyl 7-aza-2-formylbicyclo[2.2.1]heptane-7-carboxylate with a 5-membered (heterocyclyl)methyllithium followed by dehydration of the resulting alcohol will provide the desired compounds. Representative examples of 5-membered (heterocyclyl)methyllithium species are described by Micetich et al. *Can. J. Chem.* 48: 2006–2015 (1970). Other five-membered heterocycle ethenyl azabicyclic compounds can be synthesized from the trimethylsilylmethyl derivatives of 5-membered ring heterocycles. Thus, condensation of chlorotrimethylsilane with 5-membered (heterocyclyl)methyllithiums gives trimethylsilylmethyl-substituted heterocycles, which can be deprotonated with n-butyllithium. For example see Nesi, et al. *J. Organomet. Chem.* 195: 275–283 (1980). Treatment of the these carbanions with ethyl 7-aza-2-formylbicyclo[2.2.1]heptane-7-carboxylate, followed by deprotection as described previously, will lead to the desired compounds of the present invention.

Compounds of the present invention include those in which the heterocycle is a six membered ring containing at least one nitrogen atom. For example these heterocycles represented in PCT WO 97/11072 to Olesen et al. The treatment of ethyl 7-aza-2-formylbicyclo[2.2.1]heptane-7-carboxylate with 3-picolyllithium followed by dehydration and deprotection of the secondary amine will provide (E)- and (Z)-2-(2-(3-pyridyl)ethenyl)-7-azabicyclo[2.2.1]heptane. Alternatively, the treatment of ethyl 7-aza-2-formylbicyclo[2.2.1]heptane-7-carboxylate with the anion of bis(dimethylamino)phosphonylmethylpyridine followed by de-protection of the carbamate protected amine will provide (E)- and (Z)-2-(2-(3-pyridyl)ethenyl)-7-azabicyclo[2.2.1]heptane. Bis(dimethylamino)

phosphonylmethylpyridine can be synthesized according to the method by Tarasenko et al. Tett. Lett. 41: 1611–1613 (2000). (E) and (Z)-2-(2-(3-pyridyl)ethenyl)-7-azabicyclo[2.2.1]heptane may also be prepared by reaction of the lithio derivative of 3-trimethylsilylmethylpyridine with ethyl 7-aza-2-formylbicyclo[2.2.1]heptane-7-carboxylate followed by deprotection. Trimethylsilylmethylpyridine can be prepared as described in Tamao et al. *Tetrahedron* 38: 3347 (1987).

Arylethenyl-substituted azabicyclic compounds of the present invention can also be produced using palladium catalyzed coupling between an alkene and an aromatic ring. For instance, ethyl 7-aza-2-formylbicyclo[2.2.1]heptane-7-carboxylate can be treated with methylenetriphenylphosphorane to provide ethyl 7-aza-2-ethenylbicyclo[2.2.1]heptane-7-carboxylate. Palladium-catalyzed coupling reaction of a 3-bromopyridine or 3-iodopyridine with ethyl 7-aza-2-ethenylbicyclo[2.2.1]heptane-7-carboxylate followed by de-protection of the carbamate protected amine will afford (E)-2-(2-(3-pyridyl)ethenyl)-7-azabicyclo[2.2.1]heptane. Reaction conditions employing palladium(II) acetate, tri-o-tolylphosphine, and triethylamine, similar to those described by Frank et. al., *J. Org. Chem.* 43 (15): 2947–2949 (1978) and Malek et. al., *J. Org. Chem.* 47: 5395 (1982) can be used.

Arylethynyl-substituted azabicyclic compounds of the present invention can be produced in a similar manner using palladium catalyzed coupling between an alkyne and an aromatic ring. Thus, the coupling ethyl 7-aza-2-ethynylbicyclo[2.2.1]heptane-7-carboxylate with a 5-substituted 3-halo pyridine (i.e. 3-bromo-5-isopropoxypyridine) under Sonagashira reaction conditions, followed by removal of ethyl carbamate protecting group, will provide 2-(2-(3-(5-isopropoxypyridyl))ethynyl)-7-azabicyclo[2.2.1]heptane. Typically, the types of procedures set forth in K. Nakamura et. al. *Synlett:* 549 (1999), J. W. Tilley et. al. *J. Org. Chem.* 53: 386 (1988) and S. Thornrad et. al. *J. Org. Chem.* 63: 8551 (1998), involving the palladium and copper(I) catalyzed coupling of an alkyne and a halo-substituted pyridine or benzene, are used. Ethyl 7-aza-2-ethynylbicyclo[2.2.1]heptane-7-carboxylate can be prepared by treatment of ethyl 7-aza-2-formylbicyclo[2.2.1]heptane-7-carboxylate with triphenylphosphine and carbon tetrabromide followed by n-butyllithium. This can be performed as described in Eymery et al. *Synthesis:* 185–213 (2000).

Compounds of the present invention include those in which the pyridine ring is substituted (e.g., on the 5 position) with moieties that are stable to the processes used in their generation. For instance, a variety of 5-alkoxy, 5-aryloxy and 5-aryl substituents can be accommodated by the reactions described previously for the assembling of the ethenyl and ethynyl linkage between the pyridine ring and the azabicyclic unit. The 5-alkoxy- and 5-aryloxy-3-bromopyridines required for the production of these compounds can be made in various ways. In one method, 3,5-dibromopyridine is heated with an excess of sodium alkoxide or sodium aryloxide in N,N-dimethylformamide (with or without copper powder catalyst). Techniques such as those described in D. L. Comins et al., *J. Org. Chem.* 55: 69–73 (1990) and H. J. den Hertog et al., *Recl. Trav. Chim. Pays-Bas* 74: 1171–1178 (1955) can be used for this purpose. The 5-alkoxy- and 5-aryloxy-3-bromopyridines thus produced can be coupled with ethyl 7-aza-2-ethenylbicyclo[2.2.1]heptane-7-carboxylate or ethyl 7-aza-2-ethynylbicyclo[2.2.1]heptane-7-carboxylate, using palladium (II) catalysis. Alternatively, 5-alkoxy-3-bromopyridines can be generated from 5-bromonicotinic acid as follows: (i) 5-Bromonicotinic acid is converted to 5-bromonicotinamide by sequential treatment with thionyl chloride and aqueous ammonia. (ii) The resulting 5-bromonicotinamide, previously described by C. V. Greco et al., *J. Heteocyclic Chem.* 7(4): 761 (1970), is subjected to Hofmann degradation by treatment with sodium hydroxide and a 70% solution of calcium hypochlorite. (iii) The resulting 3-amino-5-bromopyridine, previously described by C. V. Greco et al., *J. Heteocyclic Chem.* 7(4): 761 (1970), can be converted to 5-alkoxy-3-bromopyridines by diazotization (with isoamyl nitrite under acidic conditions) in the presence of alcohols.

5-Aryl-3-bromopyridines, generated from Suzuki coupling of 3,5-dibromopyridine and arylboronic acids, can also be used in the palladium catalyzed reactions previously described. For instance, 5-phenyl-3-bromopyridine can be made by treatment of 3,5-dibromopyridine with phenylboronic acid in the presence tetrakis(triphenylphosphine) palladium(0). Procedures such as those described by N. Miyaura and A. Suzuki, *Chem. Rev.* 95: 2457–2483 (1995) can be used. Subsequent palladium catalyzed reaction with ethyl 7-aza-2-ethenylbicyclo[2.2.1]heptane-7-carboxylate or ethyl 7-aza-2-ethynylbicyclo[2.2.1]heptane-7-carboxylate (as previously described for 3-bromopyridine), followed by deprotection will provide the substituted pyridylethenylazabicycle or substituted pyridylethynylazabicycle. For example, palladium (II) catalyzed coupling of ethyl 7-aza-2-ethenylbicyclo[2.2.1]heptane-7-carboxylate and 5-phenyl-3-bromopyridine (followed by hydrolytic removal of the ethyl carbamate) will produce (E)-2-(2-(3-(5-phenylpyridyl))ethenyl)-7-azabicyclo[2.2.1]heptane.

Other 2-(2-(3-(5-substitutedpyridyl))ethenyl)-7-azabicyclo[2.2.1]heptanes and 2-(2-(3-(5-substitutedpyridyl))ethynyl)-7-azabicyclo[2.2.1]heptanes can be generated from commercially available 3,5-dibromopyridine, using techniques known to those skilled in the art of organic synthesis. Thus, coupling of 3,5-dibromopyridine to ethyl 7-aza-2-ethenylbicyclo[2.2.1]heptane-7-carboxylate or ethyl 7-aza-2-ethynylbicyclo[2.2.1]heptane-7-carboxylate will provide the 5-bromo derivatives, which can be used as precursors for other 5-substituted compounds. For instance, (E)-2-(2-(3-(5-bromopyridyl))ethenyl)-7-azabicyclo[2.2.1]heptane can be converted into (E)-7-tosyl-2-(2-(3-(5-bromopyridyl))ethenyl)-7-azabicyclo[2.2.1]heptane by the action of toluenesulfonyl chloride as described by S. Ji, et al., *J. Amer. Chem. Soc.* 89: 5311–5312 (1967). (E)-7-Tosyl-2-(2-(3-(5-bromopyridyl))ethenyl)-7-azabicyclo[2.2.1]heptane can then be heated with aqueous ammonia and cupric sulfate to generate the corresponding 5-amino substituted material, (E)-7-tosyl-2-(2-(3-(5-aminopyridyl))ethenyl)-7-azabicyclo[2.2.1]heptane. Such a method is reported by C. Zwart et al., *Recueil Trav. Chim. Pays-Bas* 74: 1062–1069 (1955). 5-Alkylamino substituted compounds can be prepared in a similar manner. 5-Ethynyl-substituted compounds can be prepared from the 5-bromo compound by palladium catalyzed coupling using 2-methyl-3-butyn-2-ol, followed by base (sodium hydride) catalyzed removal of the acetone unit, according to the general techniques described in N. D. P. Cosford et al., *J. Med. Chem.* 39: 3235–3237 (1996). The 5-azido substituted analogs can be prepared from the 5-bromo compound by reaction with lithium azide in N,N-dimethylformamide. 5-Alkylthio substituted analogs can be prepared from the 5-bromo compound by reaction with an appropriate sodium alkylmercaptide(sodium alkanethiolate), using techniques known to those skilled in the art of organic synthesis. The tosyl protecting group may be removed by reductive desulfonation using sodium naphthalide, as described by S. Ji, et al., *J. Amer. Chem. Soc.* 89: 5311–5312 (1967).

A number of other analogs, bearing substituents in the 5 position of the pyridine ring, can be synthesized from (E)-7-tosyl-2-(2-(3-(5-aminopyridyl))ethenyl)-7-azabicyclo[2.2.1]heptane (the synthesis of which is described above) via the 5-diazonium salt intermediate. Among the other 5-substituted analogs that can be produced from 5-diazonium salt intermediates are: 5-hydroxy analogs, 5-alkoxy analogs, 5-fluoro analogs, 5-chloro analogs, 5-bromo analogs, 5-iodo analogs, 5-cyano analogs, and 5-mercapto analogs. These compounds can be synthesized using the general techniques set forth in C. Zwart et al., *Recueil Trav. Chim. Pays-Bas* 74: 1062–1069 (1955). For example, 5-hydroxy substituted analogs can be prepared from the reaction of the corresponding 5-diazonium salt intermediates with water. 5-Alkoxy analogs can be made from the reaction of the diazonium salts with alcohols. 5-Fluoro substituted analogs can be prepared from the reaction of the 5-diazonium salt intermediates with fluoroboric acid. 5-Chloro substituted analogs can be prepared from the reaction of the 5-amino compounds with sodium nitrite and hydrochloric acid in the presence of copper chloride. 5-Cyano substituted analogs can be prepared from the reaction of the corresponding 5-diazonium salt intermediates with copper cyanide. Appropriate 5-diazonium salt intermediates can also be used for the synthesis of mercapto substituted analogs using the general techniques described in J. M. Hoffman et al., *J. Med. Chem.* 36: 953–966 (1993). The 5-mercapto substituted analogs can in turn be converted to the 5-alkylthio substituted analogs by reaction with sodium hydride and an appropriate alkyl bromide. 5-Acylamido analogs of the aforementioned compounds can be prepared by reaction of the corresponding 5-amino compounds with an appropriate acid anhydride or acid chloride using techniques known to those skilled in the art of organic synthesis.

5-Hydroxy substituted analogs of the aforementioned compounds can be used to prepare corresponding 5-alkanoyloxy substituted compounds by reaction with the appropriate acid, acid chloride, or acid anhydride. 5-Cyano substituted analogs of the aforementioned compounds can be hydrolyzed to afford the corresponding 5-carboxamido substituted compounds. Further hydrolysis results in formation of the corresponding 5-carboxylic acid substituted analogs. Reduction of the 5-cyano substituted analogs with lithium aluminum hydride yields the corresponding 5-aminomethyl analogs. 5-Acyl substituted analogs can be prepared from corresponding 5-carboxylic acid substituted analogs by reaction with an appropriate alkyl lithium using techniques known to those skilled in the art.

5-Carboxylic acid substituted analogs of the aforementioned compounds can be converted to the corresponding esters by reaction with an appropriate alcohol and acid catalyst. Compounds with an ester group at the 5-pyridyl position can be reduced with sodium borohydride or lithium aluminum hydride to produce the corresponding 5-hydroxymethyl substituted analogs. These analogs in turn can be converted to compounds bearing an ether moiety at the 5-pyridyl position by reaction with sodium hydride and an appropriate alkyl halide, using conventional techniques. Alternatively, the 5-hydroxymethyl substituted analogs can be reacted with tosyl chloride to provide the corresponding 5-tosyloxymethyl analogs. The 5-carboxylic acid substituted analogs can also be converted to the corresponding 5-alkylaminoacyl analogs by reaction with thionyl chloride and the appropriate alkylamine.

5-Tosyloxymethyl substituted analogs of the aforementioned compounds can be converted to the corresponding 5-methyl substituted compounds by reduction with lithium aluminum hydride. 5-Tosyloxymethyl substituted analogs of the aforementioned compounds can also be used to produce 5-alkyl substituted compounds via reaction with an alkyllithium. 5-Hydroxy substituted analogs of the aforementioned compounds can be used to prepare 5-N-alkylcarbamoyloxy substituted compounds by reaction with N-alkylisocyanates. 5-Amino substituted analogs of the aforementioned compounds can be used to prepare 5-N-alkoxycarboxamido substituted compounds by reaction with alkyl chloroformate esters, using techniques known to those skilled in the art of organic synthesis.

The synthesis of arylethenyl-substituted 8-azabicyclo[3.2.1]octanes and arylethynyl-substituted 8-azabicyclo[3.2.1]octanes are accomplished in a manner similar to that described for arylethenyl-substituted 7-azabicyclo[2.2.1]heptanes and arylethynyl-substituted 7-azabicyclo[2.2.1]heptanes. Treatment of pseudopelletierine (N-methyl-9-azabicyclo[3.3.1]nonan-3-one) as described earlier for tropinone (Daly et al. *Eur. J. Pharmacol.* 321:189–194 (1997)) will generate ethyl 8-aza-6-(ethoxycarbonyl)bicyclo[3.2.1]octane-8-carboxylate. Pseudopelletierine is made according to Howell et al., *Org. Syn.* Coll. Vol IV: 816–819 (1963). Reduction of ethyl 8-aza-6-(ethoxycarbonyl)bicyclo[3.2.1]octane-8-carboxylate with diisobutylaluminum hydride and subsequent reaction of the 6-formyl derivative with diethyl (5-isoxazolylmethyl)phosphonate and n-butyllithium will provide mixture of ethyl (E)- and (Z)-5-(2-(8-azabicyclo[3.2.1]oct-6-yl)ethenyl)isoxazole-8-carboxylate. Separation of the isomers followed by deprotection will provide (E)-5-(2-(8-azabicyclo[3.2.1]oct-6-yl)ethenyl)isoxazole and (Z)-5-(2-(8-azabicyclo[3.2.1]oct-6-yl)ethenyl)isoxazole. The other methods described previously for the preparation of five-membered heterocycle analogues of ethenyl-substituted 7-azabicyclo[2.2.1]heptanes may be applied similarly.

The palladium catalyzed reaction of ethyl 8-aza-6-ethenylbicyclo[3.2.1]octane-8-carboxylate (prepared by Wittig methylenation of the aldehyde) with 3-bromopyridine followed by deprotection of the amine will provide (E)- and (Z)-6-(2-(3-pyridyl)ethenyl)-8-azabicyclo[3.2.1]octane. Sonagashira reaction between ethyl 8-aza-6-ethynylbicyclo[3.2.1]octane-8-carboxylate (prepared by reaction of the aldehyde with triphenylphosphine and carbon tetrabromide followed by n-butyllithium) and 3-bromopyridine, then hydrolytic deprotection will provide 6-(2-(3-pyridyl)ethynyl)-8-azabicyclo[3.2.1]octane. Other olefinic and acetylenic derivatives can be made from 5-substituted-3-bromopyridines using methods previously described.

The synthesis of arylethenyl-substituted 9-azabicyclo[4.2.1]nonanes is accomplished in a similar manner. For instance, 9-p-toluenesulfonyl-9-aza-2-(methoxycarbonyl)bicyclo[4.2.1]non-2-ene, the synthesis of which is described by B. Trost and J. Oslob, *J. Amer. Chem. Soc.* 121: 3057–3064 (1999), serves as a suitable precursor. Reduction with diisobutylaluminum hydride will provide of 9-p-toluenesulfonyl-9-aza-2-formylbicyclo[4.2.1]nonane. Reaction of this aldehyde with diethyl (5-isoxazolylmethyl)phosphonate and n-butyllithium, then subsequent transformation as previously described, will produce (E)- and (Z)-9-p-toluenesulfonyl-5-(2-(9-azabicyclo[4.2.1]non-2-yl)ethenyl)isoxazole. Deprotection of the amine by reductive desulfonation (using sodium naphthalide, as described by S. Ji, et al., *J. Amer. Chem. Soc.* 89: 5311–5312 (1967) will provide (E)- and (Z)-5-(2-(9-azabicyclo[4.2.1]non-2-yl) ethenyl)isoxazole.

The palladium catalyzed reaction, of 9-p-toluenesulfonyl-9-aza-2-ethenylbicyclo[4.2.1]nonane (prepared by Wittig methylenation of the corresponding aldehyde) with 3-bromopyridine followed by deprotection of the amine will provide (E)- and (Z)-2-(2-(3-pyridyl)ethenyl)-9-azabicyclo [4.2.1]nonane. Sonagashira reaction 9-p-toluenesulfonyl-9-aza-2-ethynylbicyclo[4.2.1]nonane (prepared by reaction of the aldehyde with triphenylphosphine and carbon tetrabromide followed by n-butyllithium) and 3-bromopyridine, then reductive desulfonation (using sodium naphthalide, as described by S. Ji, et al., *J. Amer. Chem. Soc.* 89: 5311–5312 (1967)) will provide 2-(2-(3-pyridyl)ethynyl)-9-azabicyclo [4.2.1]nonane. Other olefinic and acetylenic derivatives can be made from 5-substituted-3-bromopyridines using methods previously described.

Other aryl ethylene substituted azabicyclic systems and aryl acetylene substituted azabicyclic systems can be generated using similar methods. For instance, the previously described ethyl 8-aza-3-oxobicyclo[3.2.1]octane-8-carboxylate (see Daly et al. *Eur. J. Pharmacol.* 321:189–194 (1997)) provides an entry into the 3-substituted 8-azabicyclo [3.2.1]octane system. Treatment with the methoxymethylene Wittig reagent will convert ethyl 8-aza-3-oxobicyclo [3.2.1]octane-8-carboxylate into ethyl 8-aza-3-formylbicyclo[3.2.1]octane-8-carboxylate. A similar use of this Wittig reagent is described by L. Jenneskens et al., *J. Org. Chem.* 51: 2162–2168 (1986). Ethyl 8-aza-3-formylbicyclo[3.2.1]octane-8-carboxylate can then be transformed, using the techniques described previously, into 3-(2-(8-azabicyclo[3.2.1]oct-6-yl)ethenyl)isoxazole or substituted versions thereof. The aldehyde can also be transformed into the corresponding alkene or alkyne and coupled to 3-bromopyridine using palladium catalysis to provide (E)-3-(2-(3-pyridyl)ethenyl)-8-azabicyclo[3.2.1]octane or 3-(2-(3-pyridyl)ethynyl)-8-azabicyclo[3.2.1]octane.

The present invention relates to a method for providing prevention of a condition or disorder to a subject susceptible to such a condition or disorder, and for providing treatment to a subject suffering therefrom. For example, the method comprises administering to a patient an amount of a compound effective for providing some degree of prevention of the progression of a CNS disorder (i.e., provide protective effects), amelioration of the symptoms of a CNS disorder, and amelioration of the recurrence of a CNS disorder. The method involves administering an effective amount of a compound selected from the general formulae, which are set forth hereinbefore. The present invention relates to a pharmaceutical composition incorporating a compound selected from the general formulae, which are set forth hereinbefore. Optically active compounds can be employed as racemic mixtures or as enantiomers. The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates. Representative pharmaceutically acceptable salts and the properties thereof are set forth in Berge et al., *J. Pharm. Sci.*, 66: 1–19 (1977) and Anderson et al., In: *The Practice Medicinal Chemistry*, Ch. 34: 739–754 (1996). Representative salts of nicotinic compounds can include those organic or inorganic acid addition salts of the type set forth in U.S. Pat. No. 5,597,919 to Dull et al., U.S. Pat. No. 5,616,716 to Dull et al. U.S. Pat. No. 5,663,356 to Ruecroft et al.; U.S. Pat. No. 5,861,423 to Caldwell et al. and U.S. Pat. No. 5,986,100 to Bencherif et al., the disclosures of which are incorporated herein by reference in their entirety. See, also, U.S. Pat. No. 3,952,050 to Price and U.S. Pat. No. 5,326,782 to Barriere et al., as well as U.S. Pat. Nos. 5,962,737 to 4,803,207 to White et al. and U.S. Pat. No. 4,528,290 to Wong et al.

Compounds of the present invention are useful for treating those types of conditions and disorders for which other types of nicotinic compounds have been proposed as therapeutics. See, for example, Williams et al. *DN&P* 7(4): 205–227 (1994), Arneric et al., *CNS Drug Rev.* 1(1): 1–26 (1995), Arneric et al., *Exp. Opin. Invest. Drugs* 5(1): 79–100 (1996), Bencherif et al., *JPET* 279: 1413 (1996), Lippiello et al., *JPET* 279: 1422 (1996), Damaj et al., *Neuroscience* (1997), Holladay et al., *J. Med. Chem* 40(28): 4169–4194 (1997), Bannon et al., *Science* 279: 77–80 (1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al the disclosures of which are incorporated herein by reference in their entirety. Compounds of the present invention can be used as analgesics, to treat ulcerative colitis, to treat a variety of neurodegenerative diseases, and to treat convulsions such as those that are symtematic of epilepsy. CNS disorders which can be treated in accordance with the present invention include presenile dementia (early onset Alzheimer's disease), senile dementia (dementia of the Alzheimer's type), HIV-dementia, multiple cerebral infarcts, Parkinsonism including Parkinson's disease, Pick's disease, Huntington's chorea, tardive dyskinesia, hyperkinesia, mania, attention deficit disorder, anxiety, depression, mild cognitive impairment, dyslexia, schizophrenia and Tourette's syndrome. Compounds of the present invention also can be used to treat conditions such as syphillis and Creutzfeld-Jakob disease.

The pharmaceutical composition also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, anticoagulants, buffering agents, anti-inflammatory agents, anti-pyretics, time release binders, anaesthetics, steroids, vitamins, minerals and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular disorder.

The manner in which the compounds are administered can vary. The compounds can be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebro ventricularly; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time-release capsule. As another example, the compounds can be delivered transdermally using the types of patch technologies available from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical formulation is administered can vary. Administration preferably is such that the active ingredients of the pharmaceutical formulation interact with receptor sites within the body of the subject that effect the functioning of the CNS. More specifically, in treating a CNS disorder administration preferably is such so as to optimize the effect upon those relevant receptor subtypes which have an effect upon the functioning of the CNS, while minimizing the effects upon muscle-type receptor subtypes. Other suitable methods for administering the compounds of the present invention are described in U.S. Pat. No. 5,604,231 to Smith et al.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject, and to activate relevant nicotinic receptor subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the reoccurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to activate relevant receptors to effect neurotransmitter (e.g., dopamine) release but the amount should be insufficient to induce effects on skeletal muscles and ganglia to any significant degree. The effective dose of compounds will of course differ from patient to patient but in general includes amounts starting where CNS effects or other desired therapeutic effects occur, but below the amount where muscular effects are observed.

Typically, the effective dose of compounds generally requires administering the compound in an amount of less than 5 mg/kg of patient weight.

Often, the compounds of the present invention are administered in an amount from less than about 1 mg/kg patent weight, and usually less than about 100 ug/kg of patient weight, but frequently between about 10 ug to less than 100 ug/kg of patient weight. For compounds of the present invention that do not induce effects on muscle type nicotinic receptors at low concentrations, the effective dose is less than 5 mg/kg of patient weight; and often such compounds are administered in an amount from 50 ug to less than 5 mg/kg of patient weight. The foregoing effective doses typically represent that amount administered as a singlee dose, or as one or more doses administered over a 24 hour period.

For human patients, the effective dose of typical compounds generally requires administering the compound in an amount of at least about 1, often at least about 10, and frequently at least about 25 ug/24 hr./patient. For human patients, the effective dose of typical compounds requires administering the compound which generally does not exceed about 500, often does not exceed about 400, and frequently does not exceed about 300 ug/24 hr./patient. In addition, administration of the effective dose is such that the concentration of the compound within the plasma of the patient normally does not exceed 500 ng/ml, and frequently does not exceed 100 ng/ml.

The compounds useful according to the method of the present invention have the ability to pass across the blood-brain barrier of the patient. As such, such compounds have the ability to enter the central nervous system of the patient. The log P values of typical compounds, which are useful in carrying out the present invention are generally greater than about −0.5, often are greater than about 0, and frequently are greater than about 0.5. The log P values of such typical compounds generally are less than about 3, often are less than about 2, and frequently are less than about 1. Log P values provide a measure of the ability of a compound to pass across a diffusion barrier, such as a biological membrane. See, Hansch, et al., *J. Med. Chem.* 11: 1 (1968).

The compounds useful according to the method of the present invention have the ability to bind to, and in most circumstances, cause activation of, nicotinic dopaminergic receptors of the brain of the patient. As such, such compounds have the ability to express nicotinic pharmacology, and in particular, to act as nicotinic agonists. The receptor binding constants of typical compounds useful in carrying out the present invention generally exceed about 0.1 nM, often exceed about 1 nM, and frequently exceed about 10 nM. The receptor binding constants of certain compounds are less than about 100 uM, often are less than about 10 uM and frequently are less than about 5 uM; and of preferred compounds generally are less than about 2.5 uM, sometimes are less than about 1 uM, and can be less than about 100 nM. Receptor binding constants provide a measure of the ability of the compound to bind to half of the relevant receptor sites of certain brain cells of the patient. See, Cheng, et al., *Biochem. Pharmacol.* 22: 3099 (1973).

The compounds useful according to the method of the present invention have the ability to demonstrate a nicotinic function by effectively activating neurotransmitter secretion from nerve ending preparations (i.e., synaptosomes). As such, such compounds have the ability to activate relevant neurons to release or secrete acetylcholine, dopamine, and other neurotransmitters. Generally, typical compounds useful in carrying out the present invention provide for the activation of dopamine secretion in amounts of at least one third, typically at least about 10 times less, frequently at least about 100 times less, and sometimes at least about 1,000 times less, than those required for activation of muscle-type nicotinic receptors. Certain compounds of the present invention can provide secretion of dopamine in an amount which is comparable to that elicited by an equal molar amount of (S)-(−)-nicotine.

The compounds of the present invention, when employed in effective amounts in accordance with the method of the present invention, are selective to certain relevant nicotinic receptors, but do not cause significant activation of receptors associated with undesirable side effects at concentrations at least greater than those required for activation of dopamine release. By this is meant that a particular dose of compound resulting in prevention and/or treatment of a CNS disorder, is essentially ineffective in eliciting activation of certain ganglia-type nicotinic receptors at concentration higher than 5 times, preferably higher than 100 times, and more preferably higher than 1,000 times, than those required for activation of dopamine release. This selectivity of certain compounds of the present invention against those ganglia-type receptors responsible for cardiovascular side effects is demonstrated by a lack of the ability of those compounds to activate nicotinic function of adrenal chromaffin tissue at concentrations greater than those required for activation of dopamine release.

Compounds of the present invention, when employed in effective amounts in accordance with the method of the present invention, are effective towards providing some degree of prevention of the progression of CNS disorders, amelioration of the symptoms of CNS disorders, an amelioration to some degree of the reoccurrence of CNS disorders. However, such effective amounts of those compounds are not sufficient to elicit any appreciable side effects, as demonstrated by increased effects relating to skeletal muscle. As such, administration of certain compounds of the present invention provides a therapeutic window in which treatment of certain CNS disorders is provided, and certain side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of CNS disorders occurs upon administration of less than ⅕, and often less than ⅒ that amount sufficient to cause certain side effects to any significant degree.

The pharmaceutical compositions of the present invention can be employed to prevent or treat certain other conditions, diseases and disorders. Exemplary of such diseases and disorders include inflammatory bowel disease, acute cholangitis, aphteous stomatitis, arthritis (e.g., rheumatoid arthritis and ostearthritis), neurodegenerative diseases, cachexia secondary to infection (e.g., as occurs in AIDS, AIDS related complex and neoplasia), as well as those indications set forth in PCT WO 98/25619. The pharmaceutical compositions of the present invention can be employed in order to ameliorate may of the symptoms associated with those conditions, diseases and disorders. Thus, pharmaceutical compositions of the present invention can be used in treating genetic diseases and disorders, in treating autoimmune disorders such as lupus, as anti-infectious agents (e.g, for treating bacterial, fungal and viral infections, as well as the effects of other types of toxins such as sepsis), as anti-inflammatory agents (e.g., for treating acute cholangitis, aphteous stomatitis, asthma, and ulcerative colitis), and as inhibitors of cytokines release (e.g., as is desirable in the treatment of cachexia, inflammation, neurodegenerative diseases, viral infection, and neoplasia), The compounds of the present invention can also be used as adjunct therapy in combination with existing therapies in the management of the aforementioned types of diseases and disorders. In such situations, administration preferably is such that the active ingredients of the pharmaceutical formulation act to optimize effects upon abnormal cytokine production, while minimizing effects upon receptor subtypes such as those that are associated with muscle and ganglia. Administration preferably is such that active ingredients interact with regions where cytokine production is affected or occurs. For the treatment of such conditions or disorders, compounds of the present invention are very potent (i.e., affect cytokine production and/or secretion at very low concentrations), and are very efficacious (i.e., significantly inhibit cytokine production and/or secretion to a relatively high degree).

Effective doses are most preferably at very low concentrations, where maximal effects are observed to occur. Concentrations, determined as the amount of compound per volume of relevant tissue, typically provide a measure of the degree to which that compound affects cytokine production. Typically, the effective dose of such compounds generally requires administering the compound in an amount of much less than 100 ug/kg of patient weight, and even less than 10 ug/kg of patient weight. The foregoing effective doses typically represent the amount administered as a single dose, or as one or more doses administered over a 24 hour period.

For human patients, the effective dose of typical compounds generally requires administering the compound in an amount of at least about 1, often at least about 10, and frequently at least about 25 ug/24 hr./patient. For human patients, the effective dose of typical compounds requires administering the compound which generally does not exceed about 1, often does not exceed about 0.75, often does not exceed about 0.5, frequently does not exceed about 0.25 mg/24 hr./patient. In addition, administration of the effective dose is such that the concentration of the compound within the plasma of the patient normally does not exceed 500 pg/ml, often does not exceed 300 pg/ml, and frequently does not exceed 100 pg/ml. When employed in such a manner, compounds of the present invention are dose dependent, and as such, cause inhibition of cytokine production and/or secretion when employed at low concentrations but do not exhibit those inhibiting effects at higher concentrations. Compounds of the present invention exhibit inhibitory effects upon cytokine production and/or secretion when employed in amounts less than those amounts necessary to elicit activation of relevant nicotinic receptor subtypes to any significant degree.

The following examples are provided to illustrate the present invention, and should not be construed as limiting the scope thereof. In these examples, all parts and percentages are by weight, unless otherwise noted. Reaction yields are reported in mole percentages.

EXAMPLE 1

Sample No. 1 is (E)-5-(2-(7-azabicyclo[2.2.1]hept-2-yl)ethenyl)isoxazole, which was prepared in accordance with the following techniques:

Ethyl 8-aza-3-oxobicyclo[3.2.1]octane-8-carboxylate

Under a nitrogen atmosphere, ethyl chloroformate (35 mL) was added drop-wise to a stirred solution of tropinone (7.00 g, 50.3 mmol) in dry tetrahydrofuran (70 mL). The reaction mixture was stirred overnight, then neutralized with a saturated aqueous sodium bicarbonate (200 mL) solution and extracted with ethyl acetate (3×50 mL). The combined ethyl acetate extracts were dried over anhydrous potassium carbonate, which was subsequently filtered off. Removal of the ethyl acetate on a rotary evaporator gave ethyl 8-aza-3-oxobicyclo[3.2.1]octane-8-carboxylate (7.70 g, 77.7%) as a light yellow, viscous oil (Daly, et al., *Euro. J. Pharmacol.* 32: 189–194 (1997)).

Ethyl 8-aza-2-bromo-3-oxobicyclo[3.2.1]octane-8-carboxylate

Under a nitrogen atmosphere, a mixture of bromine (0.95 mL, 18 mmol) and 30% hydrogen bromide in acetic acid (12 mL) was added drop-wise to a stirred solution of ethyl 8-aza-3-oxobicyclo[3.2.1]octane-8-carboxylate (3.63 g, 18.4 mmol) in dry dichloromethane (100 mL) at −10° C. The mixture was stirred for 45 min, neutralized with a saturated aqueous sodium bicarbonate solution and then extracted with dichloromethane (3×25 mL). The combined dichloromethane extracts were dried over anhydrous sodium sulfate, filtered and concentrated by rotary evaporation, to give a mixture of ethyl 8-aza-2-bromo-3-oxobicyclo[3.2.1]octane-8-carboxylate and a dibrominated derivative. Chromatography on a Merck silica gel 60 (70–230 mesh) column, with ethyl acetate:hexane (1:1) as eluant, provided a pure sample of ethyl 8-aza-2-bromo-3-oxobicyclo[3.2.1]octane-8-carboxylate (2.95 g, 58.1%) and a sample (2.00 g) that was a mixture of the desired compound and the dibromo derivative.

Ethyl 7-aza-2-(ethoxycarbonyl)bicyclo[2.2.1]heptane-7-carboxylate

To a stirred solution of ethyl 8-aza-2-bromo-3-oxobicyclo [3.2.1]octane-8-carboxylate (2.90 g,10.5 mmol) in anhydrous ethanol (20 mL), sodium (0.32 g, 14 mmol) dissolved in anhydrous ethanol (20 mL) was added, and the mixture stirred at room temperature for 45 min. Saturated aqueous ammonium chloride solution (40 mL) was added, and the mixture was extracted with ethyl acetate (4×25 mL). The combined ethyl acetate extracts were dried over anhydrous sodium sulfate, filtered, and concentrated on a rotary evaporator, leaving a light brown, viscous oil (2.40 g). Chromatography on a Merck silica gel 60 (70–230 mesh) column, with ethyl acetate:hexane (1:3) as eluant, gave ethyl 7-aza-2-(ethoxycarbonyl)bicyclo[2.2.1]heptane-7-carboxylate (1.56 g, 75.4%) as a clear viscous oil.

Ethyl 7-aza-2-formylbicyclo[2.2.1]heptane-7-carboxylate

Diisobutylaluminum hydride (4.14 mL of 1.5 M solution in toluene, 6.2 mmol) was added over a period of five minutes, drop-wise, to a stirred solution of ethyl 7-aza-2-(ethoxycarbonyl)bicyclo[2.2.1]heptane-7-carboxylate (1.50 g, 6.22 mmol) in dry toluene (20 mL) under a nitrogen atmosphere at −78° C. After 4 h at −78° C., the reaction was quenched with saturated aqueous ammonium chloride solution (10 mL) and extracted with ethyl acetate (5×15 mL). The ethyl acetate extracts were combined, dried over anhydrous magnesium sulfate, filtered, and rotary evaporated to give a light brown oil (1.0 g). Column chromatography on Merck silica gel 60 (70–230 mesh), using ethyl acetate:hexane (3:1) as eluant, afforded ethyl 7-aza-2-formylbicyclo [2.2.1]heptane-7-carboxylate (750 mg, 61.0%) as a brown oil.

5-(Bromomethyl)isoxazole

N-bromosuccinimide (21.4 g, 120 mmol), 5-methylisoxazole (9.97 g, 120 mmol) and benzoyl peroxide (2.91 g, 12.0 mmol) in carbon tetrachloride (250 mL) were heated at 80° C. for 6 h, filtered then concentrated. Distillation at reduced pressure (bp 55–60° C./1 mm Hg) provided pure product as a colorless oil (14.0 g, 72.0%).

Diethyl (5-isoxazolylmethyl)phosphonate 5-(Bromomethyl)isoxazole (5.38 g, 33.2 mmol) was stirred at 0° C. as triethylphosphite (5.7 mL, 33.2 mmol) was slowly added. The mixture was stirred at room temperature for 48 h, heated under reflux for 24 h, then concentrated. Purification by distillation at reduced pressure (bp 109–115° C./0.04 mm Hg) provided pure product as a colorless oil (6.75 g, 92.7%).

Ethyl (E)- and (Z)-5-(2-(7-azabicyclo[2.2.1]hept-2-yl)ethenyl)isoxazole-7-carboxylate n-Butyllithium (1.52 mL of 2.5 M in hexanes, 3.8 mmol,) was added to a stirred solution of diethyl-5-isoxazolylmethyl)phosphonate (0.834 g, 3.80 mmol) in dry tetrahydrofuran (10 mL) at 0° C. The mixture was stirred for 30 min, and then a solution of ethyl 7-aza-2-formylbicyclo [2.2.1]heptane-7-carboxylate (0.500 g, 2.53 mmol) in dry tetrahydrofuran (10 mL) was added. The mixture was stirred for 12 h, and was then poured onto saturated ammonium chloride solution and extracted using methylene chloride (2×50 mL). The combined methylene chloride extracts were dried (sodium sulfate) and concentrated. Purification by chromatography on Merck silica gel 60 (70–230 mesh), using ethyl acetate:hexane (1:9) as eluant, provided pure (E)-product as a colorless oil (0.103 g, 16%), pure (Z)-product as a colorless oil (0.172 g, 26%) and a mixture of (E)- and (Z)-product as a colorless oil (0.103 g, 16%)

(E)-5-(2-(7-Azabicyclo[2.2.1]hept-2-yl)ethenyl)isoxazole

Ethyl (E)-5-(2-(7-azabicyclo[2.2.1]hept-2-yl)ethenyl) isoxazole-7-carboxylate (0.173 g, 0.659 mmol) and concentrated aqueous hydrochloric acid (2 mL) were heated at reflux for 8 h. The mixture was partitioned between methylene chloride (20 mL) and water (10 mL). The aqueous portion was adjusted to pH 12 using 10% aqueous sodium hydroxide solution and extracted with methylene chloride (3×25 mL). The extracts were dried using sodium sulfate and concentrated to an oil. Purification by chromatography on Merck silica gel 60 (70–230 mesh) using methanol:chloroform (1:9) provided the desired product as a yellow oil (0.050 g, 40% yield).

EXAMPLE 2

Determination of Binding to Relevant Receptor Sites

Binding of the compounds to relevant receptor sites was determined in accordance with the techniques described in U.S. Pat. No. 5,597,919 to Dull et al. Inhibition constants (Ki values), reported in nM, were calculated from the $IC_{50}$ values using the method of Cheng et al., *Biochem, Pharmacol.* 22:3099 (1973). Low binding constants indicate that the compounds of the present invention exhibit good high affinity binding to certain CNS nicotinic receptors. The compound of Example 1 exhibits a Ki of 80 nM.

What is claimed is:

1. A compound having the structure represented by the formula:

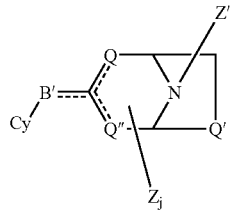

wherein Cy represents a 5 or 6 member aromatic ring or substituted 5 or 6 member aromatic ring, B' is ethylenic, or acetylenic, Q is $(CH_2)_m$, Q' is $(CH_2)_p$, and Q" is $(CH_2)_q$ where m is 1, 2, 3 or 4, p is 0, 1, 2 or 3, and q is 0, 1 or 2, and the values of m, p and q are selected such that the azabicyclic ring shown in the structure contains 7 members, and either p or q is 1;

Z represents a non-hydrogen substituent group selected from the group consisting of alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, halo, —NR'R", —CF$_3$, —OH, —CN, —NO$_2$, —C$_2$R', —SH, —SCH$_3$, —N$_3$, —SO$_2$CH$_3$, —OR', —SR', —C(=O)NR'R", —NR'C(=O)R', —C(=O)R', —C(=O)OR', —(CH$_2$)$_x$OR', —OC(=O)R', —(CR'R")$_x$OCH$_2$C$_2$R', —(CR'R")$_x$C(=O)R', —O(CR'R")$_x$C(=O)R', —C$_2$(CR'R")$_x$OR', —(CR'R")$_x$NR'R", —OC(=O)NR'R" and —NR'C(=O)OR', wherein x is an integer from 1 to 6, R' and R" are individually hydrogen or $C_1$–$C_8$ alkyl, an aromatic group-containing species or a substituted aromatic group-containing species, where the aromatic group-containing species are selected from the group consisting of pyridinyl, quinolinyl, pyrimidinyl, phenyl, and benzyl, or R' and R" can form a cycloalkyl functionality, any of the foregoing groups indicated as being substituted can be suitably substituted with at least one substituent group selected from the group consisting of alkyl, hydroxyl, alkoxy, halo, and amino substituents, j is an integer from 0 to 5, Z' represent hydrogen or lower alkyl, the dotted lines in the structure signify carbon-carbon single bonds or carbon-carbon double bonds with the proviso that where B' is alkylenic, only one dotted line represents a carbon-carbon double bond, and when B' is ethylenic or acetylenic, no dotted line represents a carbon-carbon double bond, and ethylenic is —CE'=CE"-, wherein E' and E" are hydrogen or a non-hydrogen substituent as defined above with respect to Z, and acetylenic is —C≡C—, wherein the term "substituted" as applied to the terms "substituted alkyl, substituted alkenyl, substituted heterocyclyl, substituted cycloalkyl, substituted aryl, substituted alkylaryl, arylalkyl, and substituted arylalkyl refers to one or more alkyl, hydroxy, alkoxy, halo or amino substituents.

2. The compound of claim 1 wherein Cy is:

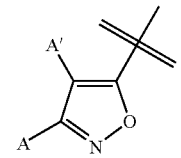

wherein A and A' individually are either hydrogen or suitable non-hydrogen substituent species selected from the group consisting of alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, halo, —NR'R", —CF$_3$, —OH, —CN, —NO$_2$, —C$_2$R', —SH, —SCH$_3$, —N$_3$, —SO$_2$CH$_3$, —OR', —SR', —C(=O)NR'R", —NR'C(=O)R', —C(=O)R', —C(=O)OR', —(CH$_2$)$_x$OR', —OC(=O)R', —(CR'R")$_x$OCH$_2$C$_2$R', —(CR'R")$_x$C(=O)R', —O(CR'R")$_x$C(=O)R', —C$_2$(CR'R")$_x$OR', —(CR'R")$_x$NR'R", —OC(=O)NR'R" and —NR'C(=O)OR', wherein x is an integer from 1 to 6, R' and R" are individually hydrogen or $C_1$–$C_8$ alkyl, an aromatic group-containing species or a substituted aromatic group-containing species, where the aromatic group-containing species are selected from the group consisting of pyridinyl, quinolinyl, pyrimidinyl, phenyl, and benzyl, or R' and R" can form a cycloalkyl functionality, and any of the foregoing groups indicated as being substituted can be suitably substituted with at least one substituent group selected from the group consisting of alkyl, hydroxyl, alkoxy, halo, and amino substituents.

3. The compound of claim 1 wherein Cy is

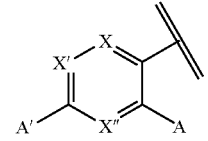

X, X' and X" are individually nitrogen, nitrogen bonded to oxygen or carbon bonded to a substituent species characterized as having a sigma m value between about −0.3 and about 0.75, A and A' individually are either hydrogen or suitable non-hydrogen substituent species having a sigma m value between about −0.3 and about 0.75, wherein substituent species having a sigma m value between about −0.3 and about 0.75 are selected from the group consisting of hydrogen, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, halo, —NR'R", —CF$_3$, —OH, —CN, —NO$_2$, —C$_2$R', —SH, —SCH$_3$, —N$_3$, —SO$_2$CH$_3$, —OR', —SR', —C(=O)NR'R", —NR'C(=O)R', —C(=O)R', —C(=O)OR', —(CH$_2$)$_x$OR', —OC(=O)R', —(CR'R")$_x$OCH$_2$C$_2$R', —(CR'R")$_x$C(=O)R', —O(CR'R")$_x$C(=O)R', —C$_2$(CR'R")$_x$OR', —(CR'R")$_x$NR'R", —OC(=O)NR'R" and —NR'C(=O)OR', wherein x is an integer from 1 to 6, R' and R" are individually hydrogen or $C_1$–$C_8$ alkyl, an aromatic group-containing species or a substituted aromatic group-containing species, where the aromatic group-containing species are selected from the group consisting of pyridinyl, quinolinyl, pyrimidinyl, phenyl, and benzyl, or R' and R" can form a cycloalkyl functionality, and any of the foregoing groups indicated as being substituted can be suitably substituted with at least one substituent group selected from the group consisting of alkyl, hydroxyl, alkoxy, halo, and amino substituents.

4. The compound of claim 3 wherein X" is nitrogen.

5. The compound of claim 3 wherein X" is selected from the group consisting of $CNO_2$, $CNH_2$, $CNHCH_3$ and $CN(CH_3)_2$.

6. The compound of claim 3 wherein X' and X" are nitrogen.

7. The compound of claim 3 wherein Cy represents a 3-pyridyl moiety.

8. A compound selected from the group consisting of:
(E)- and (Z)-5-(2-(7-azabicyclo[2.2.1]hept-2-yl)ethenyl) isoxazole and
(E)- and (Z)-5-(2-(7-azabicyclo[2.2.1]hept-2-yl)ethenyl)-3-methylisoxazole.

9. A compound selected from the group consisting of:
(E)- and (Z)-2-(2-(3-pyridyl)ethenyl)-7-azabicyclo[2.2.1] heptane,
(E)- and (Z)-2-(2-(5-methoxy-3-pyridyl)ethenyl)-7-azabicyclo[2.2.1]heptane,
(E)- and (Z)-2-(2-(5-ethoxy-3-pyridyl)ethenyl)-7-azabicyclo[2.2.1]heptane,
(E)- and (Z)-2-(2-(5-isopropoxy-3-pyridyl)ethenyl)-7-azabicyclo[2.2.1]heptane,
(E)- and (Z)-2-(2-(5-isobutoxy-3-pyridyl)ethenyl)-7-azabicyclo[2.2.1]heptane,
(E)- and (Z)-2-(2-(5-phenoxy-3-pyridyl)ethenyl)-7-azabicyclo[2.2.1]heptane,
(E)- and (Z)-2-(2-(5-benzyloxy-3-pyridyl)ethenyl)-7-azabicyclo[2.2.1]heptane,
(E)- and (Z)-2-(2-(5-methoxymethyl-3-pyridyl)ethenyl)-7-azabicyclo[2.2.1]heptane
(E)- and (Z)-2-(2-(5-phenyl-3-pyridyl)ethenyl)-7-azabicyclo[2.2.1]heptane, and
(E)- and (Z)-2-(2-(5-hydroxy-3-pyridyl)ethenyl)-7-azabicyclo[2.2.1]heptane.

10. A compound selected from the group consisting of:
2-(2-(3-pyridyl)ethynyl)-7-azabicyclo[2.2.1]heptane,
2-(2-(5-methoxy-3-pyridyl)ethynyl)-7-azabicyclo[2.2.1]heptane,
2-(2-(5-ethoxy-3-pyridyl)ethynyl)-7-azabicyclo[2.2.1]heptane,
2-(2-(5-isopropoxy-3-pyridyl)ethynyl)-7-azabicyclo[2.2.1]heptane,
2-(2-(5-isobutoxy-3-pyridyl)ethynyl)-7-azabicyclo[2.2.1]heptane,
2-(2-(5-phenoxy-3-pyridyl)ethynyl)-7-azabicyclo[2.2.1]heptane,
2-(2-(5-benzyloxy-3-pyridyl)ethynyl)-7-azabicyclo[2.2.1]heptane,
2-(2-(5-methoxymethyl-3-pyridyl)ethynyl)-7-azabicyclo[2.2.1]heptane,
2-(2-(5-phenyl-3-pyridyl)ethynyl)-7-azabicyclo[2.2.1]heptane and
2-(2-(5-hydroxy-3-pyridyl)ethynyl)-7-azabicyclo[2.2.1]heptane.

11. The compound of claim 1 wherein m is 1, 2 or 3.

12. The compound of claim 1 wherein p is 0, 1 or 2.

13. The compound of claim 1 wherein q is 0 or 1.

14. The compound of claim 1 wherein j is 0 or 1.

15. The compound of claim 1 wherein B' is ethylenic.

16. The compound of claim 1 wherein B' is acetylenic.

17. The compound of claim 1 wherein j is 0; Z' is hydrogen or lower alkyl; m is 1, 2 or 3; q is 0 or 1; p is 1 or 2; and each of E' and E" is hydrogen.

18. The compound of claim 17 wherein the sum of m and q is 3 or less.

19. The compound of claim 1 wherein Cy is 3-pyridinyl unsubstituted or substituted in the 5 and/or 6 position(s), 5-pyrimidinyl unsubstituted or substituted in the 2 position, or 3- or 5-isoxazolyl unsubstituted or substituted in the 4 and/or 5 and 3 and/or 4 positions respectively.

20. A pharmaceutical composition comprising an effective amount of a compound having the structure represented by the formula:

wherein Cy represents a 5 or 6 member aromatic ring or a substituted 5 or 6 member aromatic ring, B' is ethylenic, or acetylenic, Q is $(CH_2)_m$, Q' is $(CH_2)_p$, and Q" is $(CH_2)_q$ where m is 1, 2, 3 or 4, p is 0, 1, 2 or 3, and q is 0, 1 or 2, and the values of m, p and q are selected such that the azabicyclic ring shown in the structure contains 7 members, and either p or q is 1, Z represents a non-hydrogen substituent group selected from the group consisting of alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, halo, —NR'R", —$CF_3$, —OH, —CN, —$NO_2$, —$C_2$R', —SH, —$SCH_3$, —$N_3$, —$SO_2CH_3$, —OR', —SR', —C(=O)NR'R", —NR'C(=O)R', —C(=O)R', —C(=O)OR', —$(CH_2)_x$OR', —OC(=O)R', —$(CR'R")_x$OCH$_2$C$_2$R', —$(CR'R")_x$C(=O)R', —O$(CR'R")_x$C(=O)R', —C$_2$$(CR'R")_x$OR', —$(CR'R")_x$NR'R", —OC(=O)NR'R" and —NR'C(=O)OR', wherein x is an integer from 1 to 6, R' and R" are individually hydrogen or $C_1$–$C_8$ alkyl, an aromatic group-containing species or a substituted aromatic group-containing species, where the aromatic group-containing species are selected from the group consisting of pyridinyl, quinolinyl, pyrimidinyl, phenyl, and benzyl, or R' and R" can form a cycloalkyl functionality, any of the foregoing groups indicated as being substituted can be suitably substituted with at least one substituent group selected from the group consisting of alkyl, hydroxyl, alkoxy, halo, and amino substituents, j is an integer from 0 to 5, Z' represent hydrogen or lower alkyl, the dotted lines in the structure signify carbon-carbon single bonds and ethylenic is —CE'═CE"-, wherein E' and E" are hydrogen or a non-hydrogen substituent as defined above with respect to Z, and acetylenic is —C≡C—,
wherein the term "substituted" as applied to the terms "substituted alkyl, substituted alkenyl, substituted heterocyclyl, substituted cycloalkyl, substituted aryl, substituted alkylaryl, arylalkyl, and substituted arylalkyl refers to one or more alkyl, hydroxy, alkoxy, halo or amino substituents.

21. The pharmaceutical composition of claim 20 wherein Cy is:

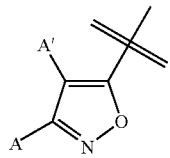

wherein A and A' individually are either hydrogen or suitable non-hydrogen substituent species selected from the group consisting of alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, halo, —NR'R", —CF$_3$, —OH, —CN, —NO$_2$, —C$_2$R', —SH, —SCH$_3$, —N$_3$, —SO$_2$CH$_3$, —OR', —SR', —C(═O) NR'R", —NR'C(═O)R', —C(═O)R', —C(═O)OR', —(CH$_2$)$_x$OR', —OC(═O)R', —(CR'R")$_x$OCH$_2$C$_2$R', —(CR'R")$_x$C(═O)R', —O(CR'R")$_x$C(═O)R', —C$_2$(CR'R")$_x$OR', —(CR'R")$_x$NR'R", —OC(═O)NR'R" and —NR'C(═O)OR',
wherein x is an integer from 1 to 6,
R' and R" are individually hydrogen or C$_1$–C$_8$ alkyl, an aromatic group-containing species or a substituted aromatic group-containing species, where the aromatic group-containing species are selected from the group consisting of pyridinyl, quinolinyl, pyrimidinyl, phenyl, and benzyl, or
R' and R" can form a cycloalkyl functionality, and
any of the foregoing groups indicated as being substituted can be suitably substituted with at least one substituent group selected from the group consisting of alkyl, hydroxyl, alkoxy, halo, and amino substituents,
j is an integer from 0 to ≡,
Z" represents hydrogen or lower alkyl, the dotted lines in the structure signify carbon-carbon single bonds and ethylenic is -CE"═ are hydrogen or a non-hydrogen substituent as defined above with respect to Z, and acetylenic is —C≡C-,
wherein the term "substituted cycloalkyl, substituted aryl, substituted alkylaryl, arylalkyl, and substituted arylalkyl refers to one or more alkyl, hydroxy, alkoxy, halo or amino substituents.

22. The pharmaceutical composition of claim 20 wherein Cy is

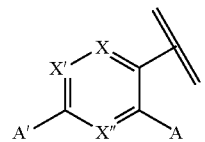

X, X' and X" are individually nitrogen, nitrogen bonded to oxygen or carbon bonded to a substituent species characterized as having a sigma m value between about −0.3 and about 0.75, A and A' individually are either hydrogen or suitable non-hydrogen substituent species having a sigma m value between about −0.3 and about 0.75,
wherein substituent species having a sigma m value between about −0.3 and about 0.75 are selected from the group consisting of hydrogen, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, halo, —NR'R", —CF$_3$, —OH, —CN, —NO$_2$, —C$_2$R', —SH, —SCH$_3$, —N$_3$, —SO$_2$CH$_3$, —OR', —SR', —C(═O)NR'R", —NR'C(═O)R', —C(═O)R', —C(═O)OR', —(CH$_2$)$_x$OR', —OC(═O)R', —(CR'R")$_x$OCH$_2$C$_2$R', —(CR'R")$_x$C(═O)R', —O(CR'R")$_x$C(═O)R', —C$_2$(CR'R")$_x$OR', —(CR'R")$_x$NR'R", —OC(═O)NR'R" and —NR'C(═O)OR',
wherein x is an integer from 1 to 6,
R' and R" are individually hydrogen or C$_1$–C$_8$ alkyl, an aromatic group-containing species or a substituted aromatic group-containing species, where the aromatic group-containing species are selected from the group consisting of pyridinyl, quinolinyl, pyrimidinyl, phenyl, and benzyl, or
R' and R" can form a cycloalkyl functionality, and
any of the foregoing groups indicated as being substituted can be suitably substituted with at least one substituent group selected from the group consisting of alkyl, hydroxyl, alkoxy, halo, and amino substituents.

23. The pharmaceuticl composition of claim 22 wherein X" is nitrogen.

24. The pharmaceuticl composition of claim 22 wherein X" is selected from the group consisting of CNO$_2$, CNH$_2$, CNHCH$_3$ and CN(CH$_3$)$_2$.

25. The pharmaceuticl composition of claim 22 wherein X' and X" are nitrogen.

26. The pharmaceuticl composition of claim 22 wherein Cy represents a 3-pyridyl moiety.

27. The pharmaceuticl composition of claim 20 wherein the compound is selected from the group consisting of:
(E)- and (Z)-5-(2-(7-azabicyclo[2.2.1]hept-2-yl)ethenyl) isoxazole and
(E)- and (Z)-5-(2-(7-azabicyclo[2.2.1]hept-2-yl)ethenyl)-3-methylisoxazole.

28. The pharmaceuticl composition of claim 20 wherein the compound is selected from the group consisting of:
(E)- and (Z)-2-(2-(3-pyridyl)ethenyl)-7-azabicyclo[2.2.1] heptane,
(E)- and (Z)-2-(2-(5-methoxy-3-pyridyl)ethenyl)-7-azabicyclo[2.2.1]heptane,
(E)- and (Z)-2-(2-(5-ethoxy-3-pyridyl)ethenyl)-7-azabicyclo[2.2.1]heptane,
(E)- and (Z)-2-(2-(5-isopropoxy-3-pyridyl)ethenyl)-7-azabicyclo[2.2.1]heptane,
(E)- and (Z)-2-(2-(5-isobutoxy-3-pyridyl)ethenyl)-7-azabicyclo[2.2.1]heptane,
(E)- and (Z)-2-(2-(5-phenoxy-3-pyridyl)ethenyl)-7-azabicyclo[2.2.1]heptane,
(E)- and (Z)-2-(2-(5-benzyloxy-3-pyridyl)ethenyl)-7-azabicyclo[2.2.1]heptane,
(E)- and (Z)-2-(2-(5-methoxymethyl-3-pyridyl)ethenyl)-7-azabicyclo[2.2.1]heptane,
(E)- and (Z)-2-(2-(5-phenyl-3-pyridyl)ethenyl)-7-azabicyclo[2.2.1]heptane, and (E)- and (Z)-2-(2-(5-hydroxy-3-pyridyl)ethenyl)-7-azabicyclo[2.2.1]heptane.

29. The pharmaceuticl composition of claim 20 wherein the compound is selected from the group consisting of:

2-(2-(3-pyridyl)ethynyl)-7-azabicyclo[2.2.1]heptane, 2-(2-(5-methoxy-3-pyridyl)ethynyl)-7-azabicyclo[2.2.1]heptane, 2-(2-(5-ethoxy-3-pyridyl)ethynyl)-7-azabicyclo[2.2.1]heptane, 2-(2-(5-isopropoxy-3-pyridyl)ethynyl)-7-azabicyclo[2.2.1]heptane, 2-(2-(5-isobutoxy-3-pyridyl)ethynyl)-7-azabicyclo[2.2.1]heptane, 2-(2-(5-phenoxy-3-pyridyl)ethynyl)-7-azabicyclo[2.2.1]heptane, 2-(2-(5-benzyloxy-3-pyridyl)ethynyl)-7-azabicyclo[2.2.1]heptane, 2-(2-(5-methoxymethyl-3-pyridyl)ethynyl)-7-azabicyclo[2.2.1]heptane, 2-(2-(5-phenyl-3-pyridyl)ethynyl)-7-azabicyclo[2.2.1]heptane and 2-(2-(5-hydroxy-3-pyridyl)ethynyl)-7-azabicyclo[2.2.1]heptane.

30. The pharmaceutical composition of claim 20 wherein m is 1, 2 or 3.

31. The pharmaceutical composition of claim 20 wherein p is 0, 1 or 2.

32. The pharmaceutical composition of claim 20 wherein q is 0 or 1.

33. The pharmaceutical composition of claim 20 wherein j is 0 or 1.

34. The pharmaceutical composition of claim 20 wherein B' is ethylenic.

35. The pharmaceutical composition of claim 20 wherein B' is acetylenic.

36. The pharmaceutical composition of claim 20 wherein j is 0; Z' is hydrogen or lower alkyl; m is 1, 2 or 3; q is 0 or 1; p is 1 or 2; and each of E' and E" is hydrogen.

37. The pharmaceutical composition of claim 36 wherein the sum of m and q is 3 or less.

38. The pharmaceutical composition of claim 20 wherein Cy is 3-pyridinyl unsubstituted or substituted in the 5 and/or 6 position(s), 5-pyrimidinyl unsubstituted or substituted in the 2 position, or 3- or 5-isoxazolyl unsubstituted or substituted in the 4 and/or 5 and 3 and/or 4 positions respectively.

* * * * *

UNITED STATES PATENT AND TRADEMARK OFFICE
CERTIFICATE OF CORRECTION

PATENT NO.       : 7,022,706 B2
APPLICATION NO.  : 10/668692
DATED            : April 4, 2006
INVENTOR(S)      : Clark et al.

It is certified that error appears in the above-identified patent and that said Letters Patent is hereby corrected as shown below:

In the Specification:

Column 5, Line 38, replace "substituents A" with -- substituents of A --.

Column 8, Line 26, delete the word "of".

Column 8, Line 33, replace "can using" with -- can be synthesized using --.

Column 8, Line 50, delete the word "the".

Column 10, Line 6, replace "Heteocyclic" with -- Heterocyclic --.

Column 10, Line 10, replace "Heteocyclic" with -- Heterocyclic --.

Column 10, Line 19, insert -- of -- between the terms "presence" and "tetrakis".

Column 12, Line 60, delete the word "of".

Column 17, Line 36, replace "an" with -- and --.

Column 17, Line 55, replace "Exemplary" with -- Examples --.

Column 18, Line 7, replace the third comma, that which appears following the closed parenthesis, with a period.

In the Claims:

In Claim 1, Column 21, Line 51, the term "represent" should be -- represents --.

In Claim 1, Column 21, Line 53, "or carbon-carbon double bonds with the proviso that where B' is alkylenic, only one dotted line represents a carbon-carbon double bond, and when B' is ethylenic or acetylenic, no dotted line represents a carbon-carbon double bond" should be deleted.

In Claim 1, Column 21, Line 61, the depicted double bond "-C=C-" should be a triple bond -- -C≡C- --.

In Claim 1, Column 21, Line 63, the open quotation mark " " " should be removed.

UNITED STATES PATENT AND TRADEMARK OFFICE
CERTIFICATE OF CORRECTION

PATENT NO. : 7,022,706 B2
APPLICATION NO. : 10/668692
DATED : April 4, 2006
INVENTOR(S) : Clark et al.

It is certified that error appears in the above-identified patent and that said Letters Patent is hereby corrected as shown below:

In Claim 1, Column 21, Line 65, delete the term "arylalkyl,".

In Claim 9, Column 23, Line 41, there should be a comma -- , -- after the named compound.

In Claim 10, Column 23, Line 65, there should be a comma -- , -- after the named compound and before the term "and".

In Claim 20, Column 24, Line 66, the word "represent" should be replaced with -- represents --.

In Claim 20, Column 24, Line 66, there should be a hard return after the comma.

In Claim 20, Column 25, Line 3, the depicted double bond "-C=C-" should be a triple bond -- -C≡C- --.

In Claim 20, Column 25, Line 5, the open quotation mark " " " should be removed.

In Claim 21, Column 25, Lines 46 through 55, the claim text following "and amino substituents" in line 45 should be deleted.

In Claim 23, Column 26, Line 32, "pharmaceuticl" should be replaced with -- pharmaceutical --.

In Claim 24, Column 26, Line 34, "pharmaceuticl" should be replaced with -- pharmaceutical --.

In Claim 25, Column 26, Line 37, "pharmaceuticl" should be replaced with -- pharmaceutical --.

In Claim 26, Column 26, Line 39, "pharmaceuticl" should be replaced with -- pharmaceutical --.

UNITED STATES PATENT AND TRADEMARK OFFICE
CERTIFICATE OF CORRECTION

PATENT NO. : 7,022,706 B2
APPLICATION NO. : 10/668692
DATED : April 4, 2006
INVENTOR(S) : Clark et al.

It is certified that error appears in the above-identified patent and that said Letters Patent is hereby corrected as shown below:

In Claim 27, Column 26, Line 41, "pharmaceuticl" should be replaced with -- pharmaceutical --.

In Claim 28, Column 26, Line 47, "pharmaceuticl" should be replaced with -- pharmaceutical --.

In Claim 29, Column 27, Line 3, "pharmaceuticl" should be replaced with -- pharmaceutical --.

In Claim 29, Column 27, Line 22, there should be a comma -- , -- after the named compound and before the term "and".

In Claim 33, Column 28, Line 8, "jis" should be replaced with -- j is --.

In Claim 36, Column 28, Line 14, "jis" should be replaced with -- j is --.

Signed and Sealed this

Third Day of June, 2008

JON W. DUDAS
*Director of the United States Patent and Trademark Office*